US00PP19912P2

(12) United States Plant Patent
Sheehan

(10) Patent No.: US PP19,912 P2
(45) Date of Patent: Apr. 14, 2009

(54) GRAPEVINE (SHEEGENE-2)

(50) Latin Name: *Vitis vinifera*
Varietal Denomination: Sheegene-2

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 0 days.

(21) Appl. No.: 12/012,441

(22) Filed: Jan. 31, 2008

(51) Int. Cl.
*A01H 5/00* (2006.01)

(52) U.S. Cl. ..... Plt./207
(58) Field of Classification Search ..... Plt./207
See application file for complete search history.

*Primary Examiner*—Annette H Para
(74) *Attorney, Agent, or Firm*—Baker Manock & Jensen, PC; Eric C. Cole

(57) ABSTRACT

A new and distinct variety of grapevine characterized by the production of large, green-colored seedless grapes that mature in late July, at least ten to fourteen days earlier than Thompson Seedless (unpatented) when grown in the San Joaquin Valley of Central California. The grapes of this new variety are produced on strong woody stems and branches and are well adapted to commercial handling.

1 Drawing Sheet

Latin name of the genius and species of the plant claimed: The claimed plant relates to a new and distinct variety of *Vitis vinifera* to be known as Sheegene-2.

Variety denomination:

The new variety of *Vitis vinifera* is the result of hybridization of Princess (unpatented), the pollen parent, and Red Globe (U.S. Plant Pat. No. 4,787), the seed parent. The new variety was first hybridized by Timothy P. Sheehan of Porterville, Calif. in the late spring of 2000. The new variety was asexually propagated in the dormant season of 2003, grafted on two vines of Harmony virus-free grape rootstock. The new variety was planted in a *Vitis vinifera* variety block located near Fowler, Calif. on the west side of Thompson Road, north of Adams Road. The new variety produces large, green-colored seedless grapes that mature at least ten to fourteen days earlier than Thompson Seedless (unpatented). The new variety has been shown to maintain its distinguishing characteristics through asexual propagation.

BACKGROUND OF THE INVENTION

The present invention relates to a new and distinct variety of grapevine that produces large, green-colored seedless grapes that mature for commercial harvesting and shipping during approximately the last week of July when grown in the San Joaquin Valley of Central California. The new invention resembles Thompson Seedless (unpatented) but the grapes produced by the new variety mature at least ten to fourteen days earlier.

SUMMARY OF THE INVENTION

The Sheegene-2 grapevine is characterized by producing large, green-colored seedless grapes that have excellent flavor and are mature for harvesting and shipment in late July when grown in the San Joaquin Valley of Central California. The new variety can be compared to Thompson Seedless (unpatented) but matures at least ten to fourteen days earlier, among other distinguishing characteristics.

BRIEF DESCRIPTION OF THE DRAWINGS

The accompanying drawing is a color photograph of the grapes produced by the subject variety; several leaves are displayed as well as a typical section. Across the top of the color photograph are two mature leaves displaying both the upper and lower surface. Across the middle of the color photograph on the left is a mature grape cluster; and to the right are two small immature grape clusters. In the middle of the color photograph, just below one of the small immature grape-clusters, are four grapes cut in half longitudinally as well as horizontally displaying the flesh and the shape of the fruit. Across the bottom of the color photograph is a mature branch with young leaves and nodes; several berries with young foliage and tendrils are also displayed.

DETAILED BOTANICAL DESCRIPTION

Referring more to the horticultural description of the new and distinct variety of grapevine, the following has been observed under the ecological conditions prevailing at the origin vineyard located near Fowler, Calif. in the San Joaquin Valley of Central California. All major color descriptions are by reference to the Dictionary of Color by Maerz & Paul, First Edition, published in 1930. Common colors names are also used in several instances.

Vine:

*Size.*—Large for four-year old vine.
*Vigor.*—Very good.
*Chilling requirements.*—Normal for grapevines in the San Joaquin Valley of Central California.
*Figure.*—Wide cordons forming a "T" shape figure.
*Production capacity.*—Very good.
*Regularity of bearing.*—Regular.

Trunk:

*Size.*—Medium to large; 8 inches [20.32 cm] in circumference, 25 inches [63.50 cm] above graft.
*Surface texture.*—Rough, shaggy.
*Color of bark.*—P1.6 I8 Slate V.
*Mature cane color.*—P1.14 L9 Bronze Beewax +.
*Nodes.*—Five nodes on canes.
*Length between nodes.*—4 inches [10.16 cm].
*Lenticel numbers.*—None.
*Shoot length.*—Short.
*Shoot shape.*—Contour drooping.

*Tendrils numbers.*—Single at nodes and on stem.
*Tendrils size.*—Variable; 1.97 to 4.72 inches [5 to 12 cm].
*Tendrils form.*—Bifurcate.
*Tendrils texture.*—Firm.
*Bud shape.*—Convex.
*Bud size.*—Small; 0.47 inches [12 mm] in width, 0.31 inches [8 mm] in length.
*Bud fruitfulness.*—Very good.

Branches:
*Size.*—Medium to large; 3½ to 4½ inches [8.89 to 11.03 cm] in circumference.
*Cordons.*—28 to 35 inches from trunk (71.12 to 88.9 cm).
*Surface.*—Slightly round.
*Color* (*One year or older wood*).—P1.7 C5 Sultana, Old Amethyst.
*Color* (*Immature branches*).—P1.20 L7 near Piquant green. Leaves:
Size.—Large.
*Density.*—Dense.
*Average length.*—5.57 to 7.30 inches [13.65 to 18.58 cm].
*Average width.*—7⅜ to 7¾ inches [18.73 to 19.69 cm].
*Form.*—Pentagonal.
*Texture* (*upper surface*).—Smooth.
*Texture* (*lower surface*).—Glabrous.
*Color* (*upward disposed surface*).—P1.23 J8 Mt. Vernon gr.
*Color* (*downward disposed surface*).—P1.20 K7 Near Piquant gr.
*Leaf vein color.*—P1.17 L7 Viridine Y.
*Marginal form.*—Slightly undulated.
*Leaf vein thickness.*—0.20 inches [5 mm].
*Leaf margin.*—Toothed.
*Glandular characteristics.*—0.
*Petiole size.*—Large.
*Petiole length.*—5.3 inches [13 cm].
*Petiole thickness.*—0.20 inches [5 mm].
*Petiole color.*—P1.17 L7 Viridine y.
*Petiole sinus form.*—Upside down 'U' shape.
*Lobe* (*average*).—Four.
*Tooth size.*—0.47 to 0.59 inches in length [12 to 15 mm], 0.59 to 0.79 inches [15 to 20 mm] in width.
*Tooth number.*—Four between lobes.
*Tooth shape.*—Convex.

Inflorescence:
*Size.*—4.52 to 4.92 inches [115 to 125 mm].
*Number per spur.*—Two (approximately).
*Number per vine.*—Many.

Flowers:
*Flower buds.*—Small.
*Flower buds surface.*—Glabrous.
*Flower buds.*—Generally profuse.
*Date of bloom.*—May 14, 2006.
*Date of full bloom.*—May 16, 2006.
*Size.*—0.16 to 0.20 inches [4 to 5 mm].
*Petals* (*color*).—P1.7 A8 Rose grey.
*Petals* (*size*).—Small, less than 2 mm.
*Pistil color.*—P1.5 H10 Rosewood.
*Date of visible berries set.*—May 18, 2006.
*Size of berries.*—0.12 inches [3 mm].

Fruit:
*Solids.*—18.2 Brix.
*Acids.*—0.52.
*Sugar/Acid ratio.*—35.0.
*Juice pH.*—3.42.
*Seeds.*—None.
*Capstem pedicel.*—0.47 to 0.59 inches [12 to 15 mm].
*Berry weight.*—5.68 grams.
*Juice color.*—Clear.
*Cluster size.*—Large.
*Cluster average length* (*not including stem*).—8.66 inches [22 cm].
*Cluster average diameter.*—7.09 inches [18 cm].
*Cluster average weight.*—11 lbs. 11 oz. [766.8 grams].
*Compactness.*—Compact.
*Cluster form.*—Conical.
*Stem* (*generally*).—2¼ inches [5.72 cm].
*Stem* (*Caliper*).—0.16 inches [4 mm].
*Berry size.*—Medium to large.
*Berry form.*—Ovate.
*Berry numbers.*—135.
*Berry size* (*average dimension along longitudinal axis*).—0.8 to 1.1 inches [25–28 cm].
*Berry size* (*average dimension along transverse axis*).—0.8 to 1.1 inches [25–28 cm].
*Berry size* (*average dimension along transverse axis*).—0.71 to 0.79 inches [18 to 20 mm].

Skin:
*Skin thickness.*—Medium.
*Texture.*—Semi-tough.
*Tendency to crack.*—None.
*Blush color.*—None.
*Ground color.*—P1.20 L7; near Piquant green.
*Pulp.*—Clear.
*Lenticels.*—None.

Flesh:
*Flesh color.*—P1.20 K6 Piquant green.
*Juice production.*—Very good.
*Flavor.*—Very good.
*Aroma.*—Very mild.
*Texture.*—Firm.
*Ripening.*—Even.
*Eating quality.*—Very good.
*Use.*—Fresh Market.
*Keeping quality.*—Good.
*Resistance to disease.*—None known.
*Resistance.*—Unknown.
*Harvesting.*—Late July to early August in the San Joaquin Valley of Central California.
*Shipping and handling qualities.*—Good.

Having thus described and illustrated our new variety of grapevine, we claim:

1. A new variety of grapevine to be known as Sheegene-2 and parts thereof, substantially as illustrated and described, characterized principally by its production of large, green-colored seedless grapes that mature at least ten to fourteen days earlier in the season of ripening than does Thompson Seedless (unpatented) that is resembles.

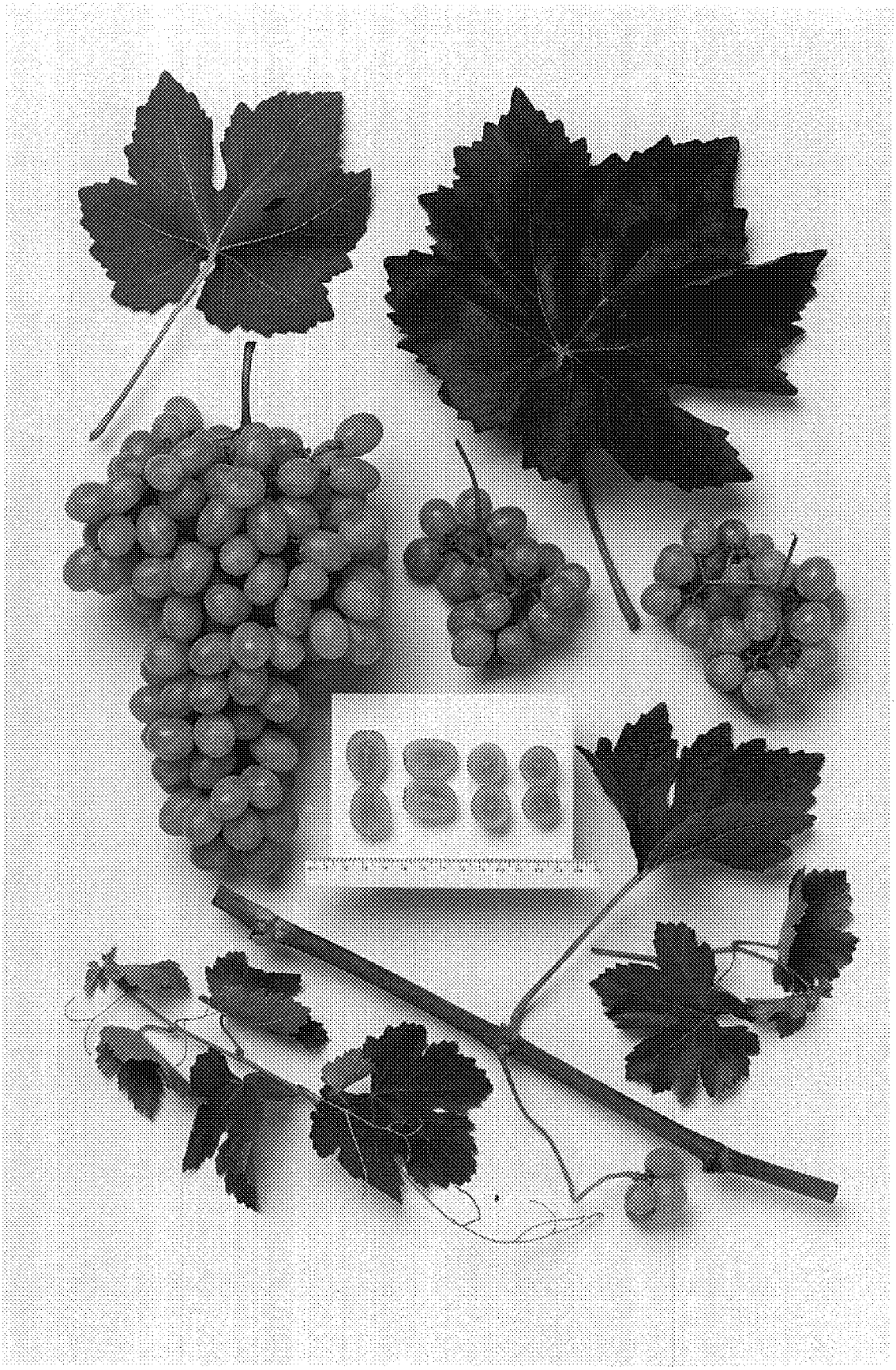

* * * * *